(12) United States Patent
Maack et al.

(10) Patent No.: US 11,213,269 B2
(45) Date of Patent: Jan. 4, 2022

(54) GEOMETRY MEASUREMENTS IN X-RAY IMAGE

(71) Applicant: KONINKLIJKE PHILIPS N.V., Eindhoven (NL)

(72) Inventors: Hanns-Ingo Maack, Norderstedt (DE); Bernd Menser, Hauset (BE); Detlef Mentrup, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 126 days.

(21) Appl. No.: 16/614,075

(22) PCT Filed: May 14, 2018

(86) PCT No.: PCT/EP2018/062421
§ 371 (c)(1),
(2) Date: Nov. 15, 2019

(87) PCT Pub. No.: WO2018/210773
PCT Pub. Date: Nov. 22, 2018

(65) Prior Publication Data
US 2021/0153833 A1 May 27, 2021

(30) Foreign Application Priority Data

May 19, 2017 (EP) .................... 17171878

(51) Int. Cl.
*A61B 6/00* (2006.01)
(52) U.S. Cl.
CPC ............ *A61B 6/5217* (2013.01); *A61B 6/466* (2013.01); *A61B 6/5282* (2013.01); *A61B 6/544* (2013.01); *A61B 6/589* (2013.01)
(58) Field of Classification Search
None
See application file for complete search history.

(56) References Cited

U.S. PATENT DOCUMENTS

2006/0198499 A1 9/2006 Spies
2007/0088209 A1 4/2007 Lötjönen
(Continued)

FOREIGN PATENT DOCUMENTS

| EP | 1349098 A1 | 10/2003 |
|---|---|---|
| WO | 2016001135 A1 | 1/2016 |
| WO | WO2016073841 A1 | 5/2016 |

OTHER PUBLICATIONS

PCT International Search Report, International application No. PCT/EP2018/062421, dated Jul. 2, 2018.

*Primary Examiner* — Hoon K Song
(74) *Attorney, Agent, or Firm* — Larry Liberchuk

(57) ABSTRACT

The present invention relates to processing X-ray images of an object. In order to improve the accuracy for interactive geometrical measurements, a device (10) for processing of an X-ray image of an object (30) is provided. The device comprises an input unit (12) and a processing unit (14). The input unit is configured to provide a shape related information (16) from an object (30) to be irradiated. The input unit is also configured to provide a generic object model (20), and to provide an actual X-ray image (18) of the object. The processing unit is configured to adapt the generic object model based on the shape related information in order to generate an individual object model (22). The processing unit is also configured to determine, based on the individual object model, an individual image processing modificator (24) for processing at least one part of the X-ray image, and to apply the individual image processing modificator for further processing of the X-ray image.

15 Claims, 3 Drawing Sheets

(56) References Cited

U.S. PATENT DOCUMENTS

2016/0104280 A1* 4/2016 Buelow .................. G06T 7/33
  382/131
2016/0140721 A1 5/2016 Kawamura
2016/0278721 A1 9/2016 Im
2019/0021682 A1* 1/2019 Mawdsley ............ G16H 50/30

* cited by examiner

GEOMETRY MEASUREMENTS IN X-RAY IMAGE

FIELD OF THE INVENTION

The present invention relates to a device for processing of an X-ray image of an object, an X-ray imaging system, and a method for processing of an X-ray image.

BACKGROUND OF THE INVENTION

It is common practice that orthopedic surgeons and others perform geometric measurements in X-ray images. In a 2D X-ray image, the spatial information of the image object is reduced from three dimensions in reality to a 2D projection. The missing third dimension may limit quantitative analysis of the image content, e.g. in a geometrical sense. For example, quantitative measurements such as bone length measurements may be carried out. Instead of rough assessments, further X-ray image may be acquired from a different point of view to achieve three-dimensional image information in order to be able to achieve improved quantitative analysis. However, it has been shown that additional X-ray imaging may lead to an increased radiation dose and may also be cumbersome in the workflow.

US2016/0104280A1 describes means for linking breast lesion locations across imaging studies. In particular, a generic three-dimensional representation of the female breast is used. Automatic translation of the lesion location into standard clinical terminology and aligning the breast model with individual patient images is comprised. Moreover, a mechanism for linking image locations showing a lesion to a location in the breast model is presented. If desired, a region of interest can be calculated by a region of interest definition module that predicts a region of interest of a known lesion in terms of the breast model representation in a new imaging study.

US2006/0198499A1 relates to a method of adapting imaging parameters for a computer tomographic radiograph of a body volume, comprising the following steps: obtaining a three-dimensional pilot radiograph with a low dose of radiation; determining a region of interest and a desired image quality in the pilot radiograph with the aid of a patient model or interactively; determining optimal imaging parameters; generating an X-ray image using the determined imaging parameters. Optionally, the X-ray image is combined with the pilot radiograph.

SUMMARY OF THE INVENTION

There may be a need to provide an improved image processing.

The object of the present invention is solved by the subject-matter of the independent claims; further embodiments are incorporated in the dependent claims. It should be noted that the following described aspects of the invention apply also for the device for processing of an X-ray image of an object, for the X-ray imaging system, and for the method for processing of an X-ray image.

In an aspect, there is provided a device for processing an X-ray image of an object as defined in appended claim 1.

In another aspect, there is provided an X-ray imaging system as defined in appended claim 5.

In another aspect, there is provided a method for processing of an X-ray image of an object as defined in appended claim 6.

In other aspects there is provided a computer program element and a computer readable medium as defined in appended claims 12 and 13.

According to the invention, a device for processing of an X-ray image of an object is provided. The device comprises an input unit and a processing unit. The input unit is configured to provide a shape related information from an object to be irradiated, a generic object model and an actual X-ray image of the object. The processing unit is configured to adapt the generic object model based on the shape related information in order to generate an individual object model. The device determines, based on the individual object model, an individual image processing modificator for processing at least one part of the X-ray image and applies the individual image processing modificator for further processing of the X-ray image.

As a result, an improved geometry measurement in X-ray imaging is provided that allows an improved further processing of the image data.

The term "shape related information" can also be referred to as "depth related information".

The term "X-ray image" can also be referred to as "X-ray image data".

The term "individual object model" can also be referred to as an "adapted object model" or an "individually adapted object model".

The term "generic object model" can also be referred to as "generic object model data".

For example, the accuracy of bone length measurements is affected by uncertainties about the magnification factor which is due to the cone-beam geometry of the X-ray beam and the unknown distance of the bone to the detector plane.

Based on the X-ray image, one can scale stored 3D-data of an artificial numerical object in a way that this model comes close to the X-ray image data.

Based on this model, one can estimate at what distance to the detector the object has been.

The shape of high contrast object (e.g. bones) can be estimated locally and this information may be used for image (post-) processing, or image-modification, e.g. image enhancement or advanced scatter estimation with shape-adaptive scatter kernel.

According to an example, the processing unit is configured to convert X-ray image data in a predetermined area of the X-ray image into specific transmission values based on actually applied X-ray radiation parameters and to determine the shape related information based on the specific transmission values.

The term "X-ray radiation parameters" relates to, for example, settings applied for generating the X-ray radiation, such as voltage, current and time.

For example, the predetermined area is selected based on empirical data to provide an object area suitable for calculating a so-called water equivalent thickness.

According to an aspect, the shape information data is determined via a range measurement unit determining the actual distance of the object to the detector.

In an example, the range measurement unit is provided as a ruler.

The range measurement unit may also be provided as a laser rangefinder.

In an example, the range measurement unit may also be provided as a range camera.

According to an example, the device for processing of an X-ray image of an object further comprises an output unit. The output unit is configured to display a result of the further processing based on the applied individual image processing modificator for processing the X-ray image.

According to the invention, also an X-ray imaging system is provided. The X-ray imaging system comprises an X-ray imaging arrangement with an X-ray source and an X-ray detector and a device for processing of an X-ray image of an object according to one of the examples above. The X-ray imaging arrangement is provided to generate the actual X-ray image of the object arranged between the X-ray source and the X-ray detector.

In an example, the device for processing of an X-ray image of an object is configured to interpret the actual X-ray image.

The term "X-ray imaging system" can also be referred to as "Picture Archiving and Communication System (PACS)".

According to the invention, also a method for processing of an X-ray image of an object is provided. The method comprises the following steps:

a1) providing a shape related information from an object to be irradiated;
a2) providing generic object model data;
b) adapting the generic object model data based on the shape related information to generate an individual object model;
c) determining, based on the individual object model, an individual image processing modificator for processing at least one part of an X-ray image;
d) providing an actual X-ray image of the object; and
e) applying the individual image processing modificator for further processing.

According to an example, in step e), the individual image processing modificator comprises an image-modification, e.g. improved scatter correction.

In an example, the method is referred to as a method for image-modification, e.g. a method for scatter correction of an X-ray image.

According to an example, in step e), the further processing comprises an image interpretation, e.g. a feature analysis.

In an example, the method is referred to as a method for image interpretation, e.g. a method for feature analysis of an X-ray image.

In an example, the individual image processing modificator is adapted to modify the X-ray image.

In another example, the individual image processing modificator can also be referred to as correction factor, or as magnification factor, or as adjustment factor, or as adaption factor.

According to an example, for providing the shape related information, the following is provided:

Converting, in a predetermined area, the X-ray image data into specific transmission values on actually applied X-ray radiation parameters.
Determining the shape related information.
The shape related information is determined based on the specific transmission values.

In an embodiment, the steps of the method for processing of an X-ray image of an object can also be referred to as:
Converting the image into transmission values using also the exposition data like kV and mAs.
Calculating the body thickness from the transmission.
Segmenting the organs like bones or lungs in the image.
Estimating a 3D-body fitting to the data. This artificial patient matches the image in terms of Transmission and the x- and y-dimensions of the segmented organs.
Calculating the typical magnification factors for the segmented organs. When measuring distances in the original image, use the magnification factors from the matching artificial patient.

In an additional feature, the volume, weight or dimensions of the fitted artificial organ could be displayed.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
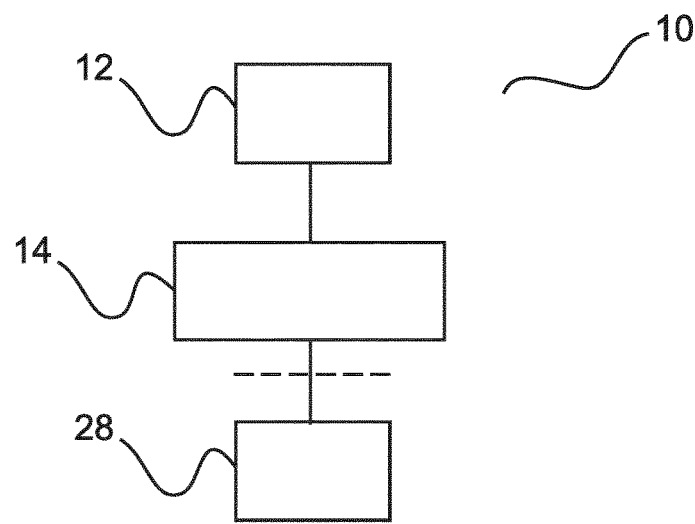
FIG. 1 shows a schematic setup of an example of a device for processing of an X-ray image of an object.

FIG. 1 shows a device 10 for processing of an X-ray image of an object. The device comprises an input unit 12 and a processing unit 14. In an option, the device 10 further comprises an output unit 28 (as indicated by a dashed separator line.

Figure 4:
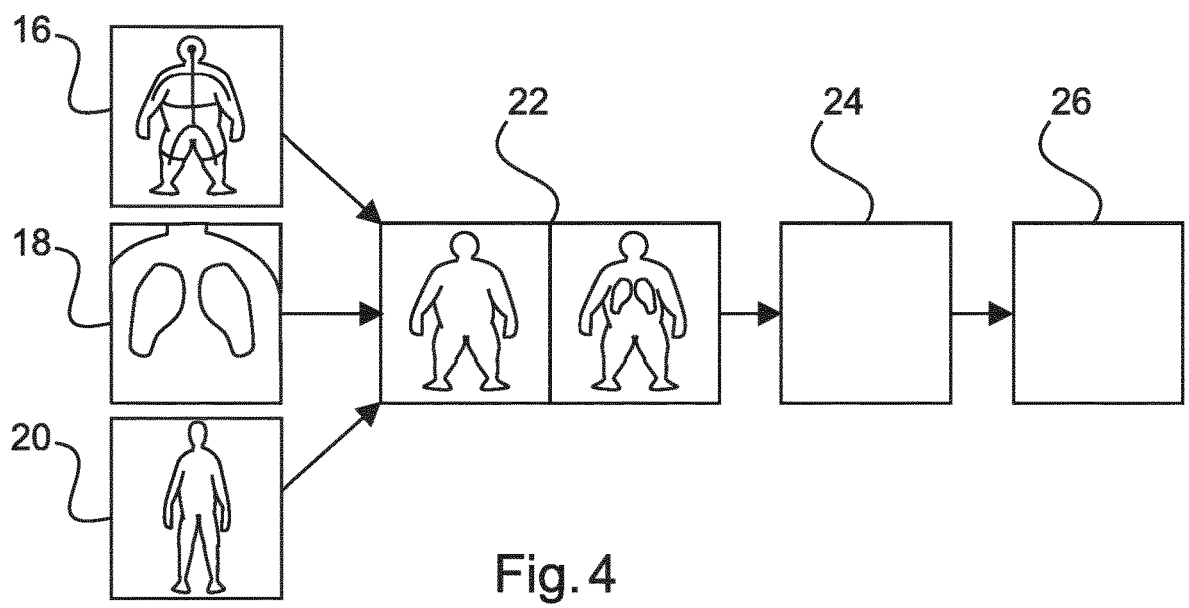
FIG. 4 shows a flowchart of an example of processing of an X-ray image of an object.

Also with reference to FIG. 4, illustrating a flowchart in relation with an optional example, the input unit 12 is configured to provide a shape related information 16 from an object 30 to be irradiated, and a generic object model 20, and to provide an actual X-ray image 18 of the object. The processing unit 14 is configured to adapt the generic object model based on the shape related information 16 in order to generate an individual object model 22. The processing unit 14 is configured to determine, based on the individual object model 22, an individual image processing modificator 24 for processing at least one part of the X-ray image, and to apply the individual image processing modificator 24 for processing the X-ray image for feature analysis 26.

In an option, the device 10 further comprises an output unit 28. The output unit 28 is configured to display a modified X-ray image for feature analysis.

In an example not shown, the processing unit 14 is configured to convert image data in a predetermined area of the X-ray image 18 into specific transmission values based on actually applied X-ray radiation parameters. The processing unit 14 is also configured to determine the shape related information 16 based on the specific transmission values.

In another example not shown, the shape related information 16 is determined via a range measurement unit determining the actual distance of the object to the detector.

Figure 2:
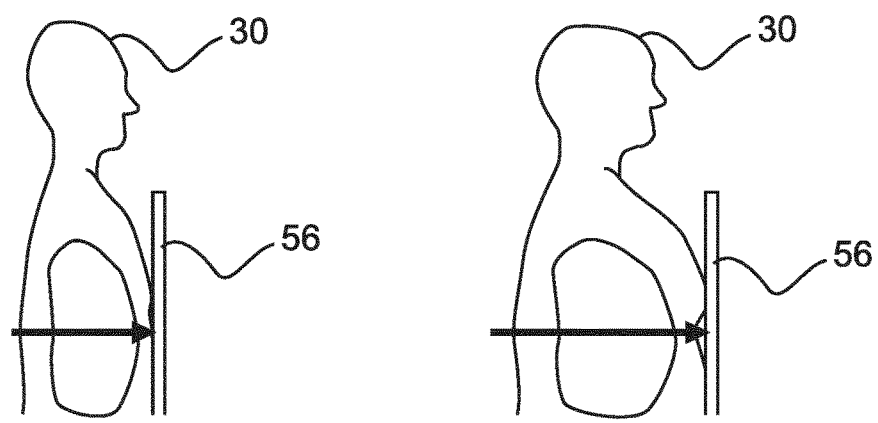
FIG. 2 shows two schematic views of a lateral view of a slim and an obese patient and a detector.

FIG. 2 shows two lateral views of patients, i.e. the object 30, and an example of an X-ray detector 56. The arrows indicate X-ray beams which pass through soft tissue layers of similar thickness in both cases, resulting in similar attenuation values. However, the lung volume of the patient on the left side is smaller than the lung volume of the patient on the right side.

Figure 3:
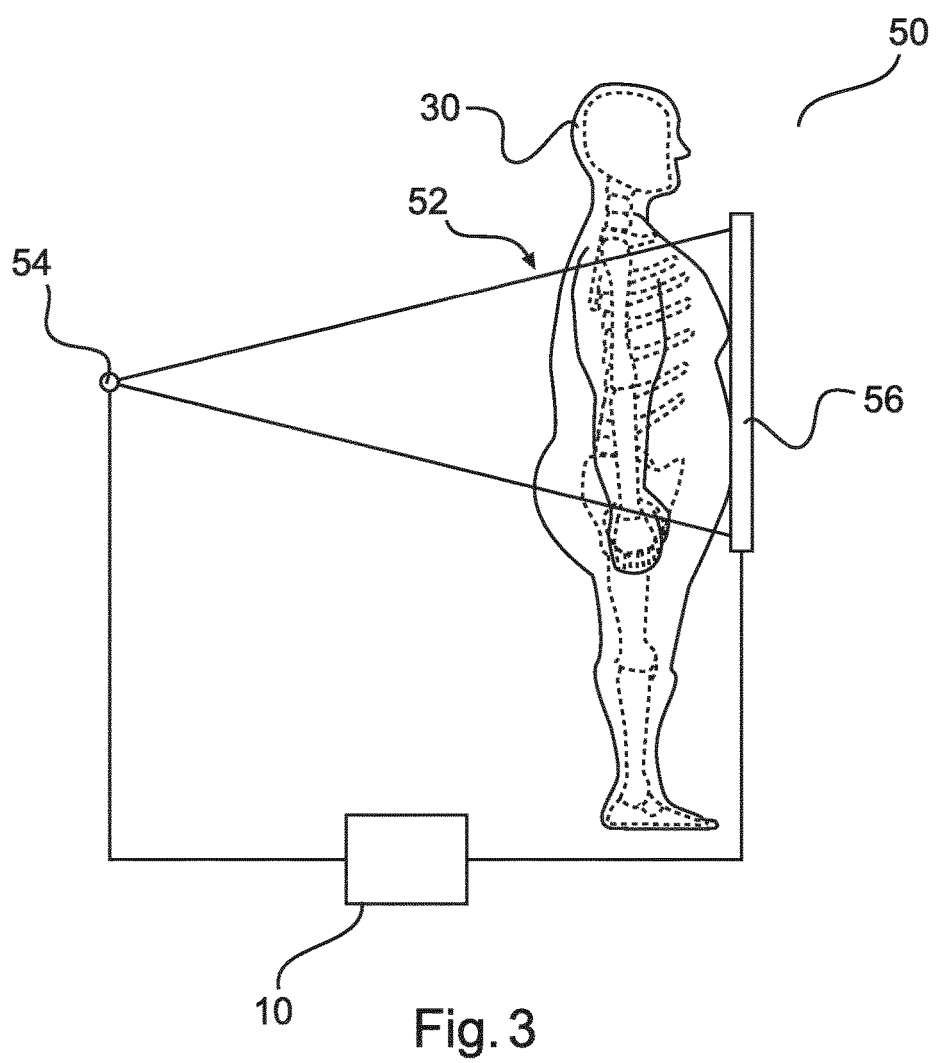
FIG. 3 shows a schematic setup of an example of an X-ray imaging system.

FIG. 3 shows an X-ray imaging system 50 for imaging an object, for example a patient (indicated with numeral 30). The system provides a space or region or area, in which the patient is arranged for imaging purposes. This space is referred to as an object receiving space 52. The system further comprises an X-ray imaging arrangement with an X-ray source 54 and the X-ray detector 56, and an example of the device 10 for processing of an X-ray image of an object.

The object receiving space 52 is arranged between the X-ray source 54 and the X-ray detector 56 to receive an object to be irradiated.

The X-ray imaging arrangement is provided to generate an actual X-ray image 18 of the object 30, and the device 10 for processing of an X-ray image of an object 30 is configured to handle the actual X-ray image 18.

The X-ray source 54 unit generates an X-ray beam to irradiate the object 30 to acquire an X-ray image 18 via the X-ray detector 56.

The processing unit 14 creates an individual generic anatomical model which takes an actual distance of the source-side of the object to the object abutting surface into account to generate shape information 16 of the object to be irradiated.

FIG. 4 shows a flowchart of a further example for processing of an X-ray image 18 of an object. In an embodiment, shape related information 16 from an object sensor is combined with a generic object model 20 including organ models, and the acquired X-ray image 18. An object modelling step uses the individual object model 22 and the X-ray image 18 to adapt the individual processing modificator 24. The individual processing modificator 24 provides 3D information that can be used for advanced post-processing or modification tasks and/or interpretation, e.g. feature analysis 26.

Figure 5:
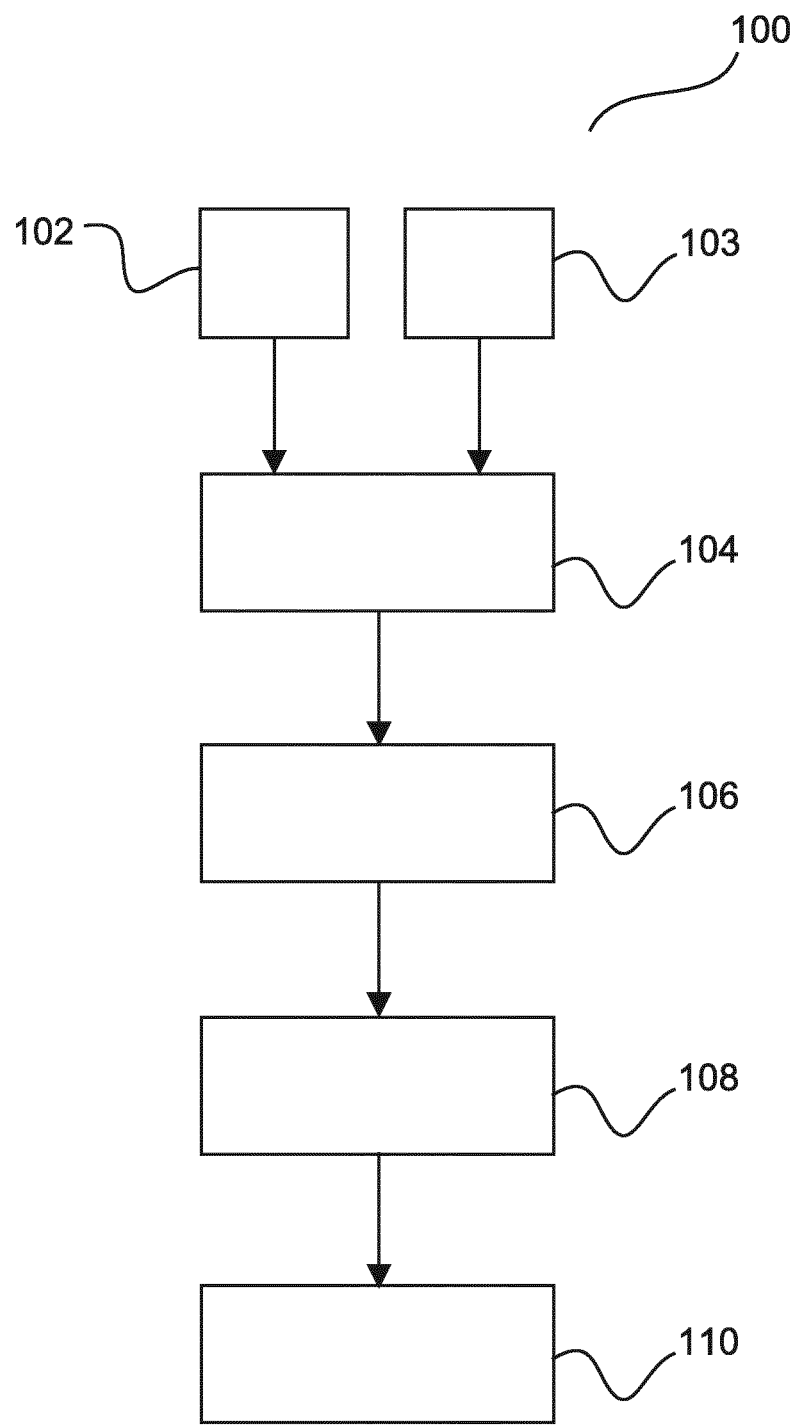
FIG. 5 shows an example of a method for processing of an X-ray image of an object.

FIG. 5 shows a method 100 for processing of an X-ray image of an object, comprising the following steps. In a first set of steps 102, 103, also referred to as step a1) and a2), a shape related information 16 from an object 30 to be irradiated (a1) and generic object model data 20 (a2) are provided. In a second step 104, also referred to as step b), the generic object model data 20, is adapted, based on the shape related information, to generate an individual object model 22. In a third step 106, also referred to as step c), based on the individual object model 22, an individual image processing modificator 24 for processing at least one part of an X-ray image 18 is determined. In a fourth step 108, also referred to as step d), an actual X-ray image 18 of the object is provided. In a fifth step 110, also referred to as step e), the individual image processing modificator for processing the X-ray image data for feature analysis is provided.

In an example, not shown, for providing the shape related information 16, the method comprises the following steps:
converting, in a predetermined area, the X-ray image 18 into specific transmission values on actually applied X-ray radiation parameters; and
determining the shape related information 16.

The shape related information 16 is determined based on the specific transmission values.

In another example, not shown, wherein, for providing the shape related information 16, the following steps are provided:
determining an actual distance of the X-ray source 54 and the object 30 to be irradiated with a range measurement unit.

A range measurement unit is arranged to determine the distance between the source (54) and the object (30) to be irradiated.

In another example, not shown, the range measurement unit is configured as a stereo camera.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for processing a 2D X-ray image of an object, comprising:
    an input; and
    a processor;
    wherein the input is configured to provide a shape related information from an object to be irradiated, provide a generic object model, provide an actual 2D X-ray image of the object;
    wherein the processor is configured to adapt the generic object model based on the shape related information in order to generate an individual object model;
    wherein the processor is configured to determine, based on the individual object model, an adapted individual image processing modificator that provides 3D information relating to the object for processing at least one part of the 2D X-ray image, wherein 3D data of an artificial numerical object is scaled such that the 3D data of the artificial numerical object is adapted towards 2D X-ray image data of the 2D X-ray image; and
    the adapted individual image processing modificator is applied for further processing of the 2D X-ray image.

2. The device according to claim 1, wherein the processor is configured to convert image data in a predetermined area of the X-ray image into specific transmission values based on actually applied X-ray radiation parameters, and determine the shape related information based on the specific transmission values.

3. The device according to claim 1, wherein the shape related information is determined via a range measurement determining the actual distance of the object to the detector.

4. The device according to claim 1, further comprising an output configured to display a result of the further processing based on the applied individual image processing modificator for processing the X-ray image.

5. An X-ray imaging system, comprising:
    an X-ray imaging arrangement comprising an X-ray source and an X-ray detector; and
    a device for processing a 2D X-ray image of an object, comprising:
        an input; and
        a processor;
        wherein the input is configured to provide a shape related information from an object to be irradiated, provide a generic object model, provide an actual 2D X-ray image of the object;
        wherein the processor is configured to adapt the generic object model based on the shape related information in order to generate an individual object model;
        wherein the processor is configured to determine, based on the individual object model, an adapted individual image processing modificator that provides 3D information relating to the object for processing at least one part of 2D the X-ray image, wherein 3D data of an artificial numerical object is scaled such that the 3D data of the artificial numerical object is adapted towards 2D X-ray image data of the 2D X-ray image; and the adapted individual image processing modificator is applied for further processing of the 2D X-ray image;
    wherein the X-ray imaging arrangement is provided to generate the actual 2D X-ray image of the object arranged between the X-ray source and the X-ray detector.

6. A method for processing a 2D X-ray image of an object, comprising:
    providing a shape related information from an object to be irradiated;
    providing generic object model data;
    adapting the generic object model data based on the shape related information to generate an individual object model;
    determining, based on the individual object model, an adapted individual image processing modificator that provides 3D information relating to the object for processing at least one part of 2D X-ray image, wherein 3D data of an artificial numerical object is scaled such that the 3D data of the artificial numerical object is adapted towards 2D X-ray image data of the 2D X-ray image;
    providing an actual 2D X-ray image of the object; and
    applying the adapted individual image processing modificator for further processing of the 2D X-ray image.

7. The method according to claim 6, wherein the further processing comprises an image modification that comprises an improved scatter correction.

8. The method according to claim 6, wherein the further processing comprises an image interpretation that comprises a feature analysis.

9. The method according to claim 6, further comprising:
    converting, in a predetermined area, the X-ray image into specific transmission values based on actually applied X-ray radiation parameters; and
    determining the shape related information based on the specific transmission values.

10. The method according to claim 6, further comprising:
    determining an actual distance between a source and the object to be irradiated using a range measurement.

11. The method according to claim 10, wherein the range measurement is determined with a stereo camera.

12. A non-transitory computer-readable medium having one or more executable instructions stored thereon which, when executed by at least one processor, cause the at least one processor to perform a method for processing a 2D X-ray image of an object, comprising:
    providing a shape related information from an object to be irradiated;
    providing generic object model data;
    adapting the generic object model data based on the shape related information to generate an individual object model;
    determining, based on the individual object model, an adapted individual image processing modificator that provides 3D information relating to the object for processing at least one part of a 2D X-ray image, wherein 3D data of an artificial numerical object is scaled such that the 3D data of the artificial numerical object is adapted towards 2D X-ray image data of the 2D X-ray image;

providing an actual 2D X-ray image of the object; and applying the adapted individual image processing modificator for further processing of the 2D X-ray image.

13. The non-transitory computer-readable medium according to claim 12, wherein the at least one processor further causes:

converting, in a predetermined area, the X-ray image into specific transmission values based on actually applied X-ray radiation parameters; and determining the shape related information based on the specific transmission values.

14. The non-transitory computer-readable medium according to claim 12, wherein the at least one processor further causes:

determining an actual distance between a source and the object to be irradiated using a range measurement.

15. The non-transitory computer-readable medium according to claim 14, wherein the range measurement is determined with a stereo camera.

* * * * *